United States Patent [19]

Hultman et al.

[11] Patent Number: 5,767,159
[45] Date of Patent: Jun. 16, 1998

[54] METHOD OF INCREASING CREATINE SUPPLY DEPOT

[76] Inventors: Eric Hultman, St. Eriksgatan 79, S-113, 32 Stockholm, Sweden; Roger C. Harris, 4 Armstrong Close, Newmarket, Suffolk CB8 8HD, United Kingdom

[21] Appl. No.: 374,691
[22] PCT Filed: Jul. 15, 1993
[86] PCT No.: PCT/SE93/00631
  § 371 Date: Jan. 24, 1995
  § 102(e) Date: Jan. 24, 1995
[87] PCT Pub. No.: WO94/02127
  PCT Pub. Date: Feb. 3, 1994

[30] Foreign Application Priority Data

Jul. 24, 1992 [GB] United Kingdom .................. 9215746

[51] Int. Cl.⁶ .................................................. A61K 31/195
[52] U.S. Cl. ...................................................... 514/565
[58] Field of Search ...................................... 514/565

[56] References Cited

U.S. PATENT DOCUMENTS

| | | | |
|---|---|---|---|
| 4,371,521 | 2/1983 | Izrael | 424/94 |
| 5,077,313 | 12/1991 | Lubec | 514/565 |
| 5,091,404 | 2/1992 | Elgebaly | 514/401 |
| 5,308,627 | 5/1994 | Umbdenstock, Jr. | 424/639 |
| 5,332,579 | 7/1994 | Umbdenstock | 424/639 |
| 5,391,550 | 2/1995 | Camiglia et al. | 514/23 |
| 5,397,786 | 3/1995 | Simone | 514/300 |

FOREIGN PATENT DOCUMENTS

| | | |
|---|---|---|
| 0199117 | 10/1986 | European Pat. Off. . |
| 0222257 | 5/1987 | European Pat. Off. . |
| 0449787 | 10/1991 | European Pat. Off. . |
| 9107954 | 6/1991 | WIPO . |

OTHER PUBLICATIONS

Medline abstract AN 92032729, Pastoris et al. Journal of Cardiothoracid and vascular anesthesia (5(5)475–80.), Oct. 1991.
Paul C. Greenhahaff et al. Influence of Oral Cratine ... Man. Clinical Science, vol. 84, pp. 565–571, Feb. 1993.
Roger C. Harris et al. Elevation of creatine ... supplementation Clinical Science, vol. 83, pp. 367–374, May 1992.
F. Busi et al. Evaluation of the hemodynamic effects of acute infusion ... phosphates. Clin Ter (Italy), vol. 111, (5), pp. 427–433, Dec. 15, 1984.
M. Marchetti et al. Electromyographic Study of Long–Term ... Disorders. Clin Ter vol. 114 (6), pp. 489–494, 1985.
Moerland et al. Administration of a creatine analog induces ... muscle 13–Mammalian Biochem., vol. 111, 1989.
Borgoglio et al. Time–course of the effect of intravenously ... heart, Chemical Abstracts vol. 99, 1983.
Lapshin, A. S., Content of Phospholipids ... sheep, Chemical Abstracts, vol. 104, 1986.

*Primary Examiner*—Keith MacMillan
*Attorney, Agent, or Firm*—Browdy and Neimark

[57] ABSTRACT

The invention relates generally to a method of increasing creatine supply depot of mammals having no disorders in the creatine metabolism, viz. Healthy, thereby increasing muscular strength, shortening the period of re-establishment of phosphorous compounds in energy after work and increasing the body of the muscles. This is achieved by the administration of creatine to the mammals in an amount of at least 15 grams, or 0.2–0.4 g/kg body weight or preferably about 0.3 g/kg body weight, per day for at least 2 days. The invention describes the use of creatine for the manufacturing of a preparation to increase the muscle performance ability in an amount which supplies a daily dose as stated above and a method.

8 Claims, 5 Drawing Sheets

METHOD OF INCREASING CREATINE SUPPLY DEPOT

DESCRIPTION OF THE INVENTION

The invention relates generally to a preparation for increasing muscle performance ability in mammals having no disorders in creatine metabolism, and thereby increasing muscular strength, shortening the period of re-establishment of phosphorous compounds in energy after work and increasing the body of the muscles. This is achieved by the administration of creatine to the mammals in an amount of at least 15 grammes, or 0.2–0.4 g/kg body weight or preferably about 0.3 g/kg body weight, per day for at least 2 days. The invention describes the use of creatine for the manufacturing of a prepara- tion comprising creatine in an amount which supplies a daily dose as stated above, as well as a method for increasing muscle per- formance ability in mammals having no disorder in creatine metabolism by supplying a daily dosage of at least 15 grammes, or 0.3 g/kg body weight, optionally divided in several doses.

BACKGROUND OF THE INVENTION

It is well established that creatine phosphate is the substrate in muscular tissue which gives the fastest resynthesis of ATP (adenosine triphosphate) and through this is used at maximum or nearly maximum power production. The resynthesis speed of ATP is nearly twice as high from creatine phosphate than from glycogen (the carbohydrate in muscle) and we have been able to show that muscle contraction with maximum power depletes the creatine phosphate supply (Hultman et al Biochem. Soc. Trans 1991; 19, 347–354). Even the oxidative resynthesis of energy substrate after work is effected positively by increased creatine amounts in the muscle tissue. It has therefore been suggested that a positive relationship exists between the amount of creatine in the muscle and the power production on repeated work with short breaks for resting.

Creatine is not sythesized in muscle tissue but is supplied to the muscle via the blood stream - partly from synthesis in liver, kidney and pancreas, and partly from the intake via food. The blood concentration of creatine is in the order of 50 µmol per liter blood and from this level a creatine uptake to the muscle tissue takes place via an active transport. The creatine excretion in the form of creatinine varies with the size of the muscle mass and reaches 0.2–2 g per day in a normal weight person.

Attempts have been made to improve the muscle power by increasing the creatine content in muscle. Creatine has been administered in different forms and in combination with other substances in different forms and in combination with other substances, such as Royal Jelly, carnosine, vitamins and amino acid compounds. Also creatine phosphate has been administered. In these attempts daily doses corresponding to 100 mg up to several grammes have been administered. This method of dosage of creatine produces moderate increases in the blood level of creatine but no measurable increases of the creatine content of the muscle (own experiments).

EP 199 117 discloses phosphocreatine as active ingredient in a parenteral preparation for the treatment of cardiac infarct and to protect the cardiac muscle (myocardium) during heart surgery. The preparation is stated to comprise 3–35 mmol disodium phosphocreatine. Example 3 discloses the use of 6 g phosphocreatine day 1 and thereafter treatment with 2 g/day during day 1 to 7.

EP 222 257 discloses compositions containing phosphocreatine to be used in therapy against cardiac diseases in amounts of 200 to 400 mg/kg/day.

WO 91/07954 relates to the use of guanidino acetic acid as a creatine precursor to achieve high intracellular muscular content of creatine in the skeletal and cardiac muscular cells. However, the applicant states at p. 2, lines 14 to 18, that "the administration of exogenous creatine does not bring any positive result, because exogenous creatine inhibits the synthesis of endogenous creatine for a quantity equal to the quantity of the creatine administered.

From U.S. Pat. No. 5,091,404 a method is previously known for preserving and/or restoring the physiological function of in vivo animal muscle tissue subject to ischaemia, comprising administration of cyclocreatine by injection or infusion in dosages from 2 g/70 kg body weight to more than 6 g/70 kg body weight, preferably 8–12 g/70 kg of body weight.

EP A2 No. 0 449 787 relates to a pharmaceutical, dietic or veterinary composition containing carnosine or peptides related thereto as the active ingredient. Examples of beneficial effects include athletic performance, improvement in persons subjected to prolonged efforts and improvements of muscular functional capacity in elderly or weakened subjects, and in children etc. Optional active ingredients may be present to provide a suitable supply. For instance creatine may be administered in dosages from 0.5 to 10 g per day. Examples of formulations include single-dose sachets containing powders or granulates which may optionally be effervescent and may be dissolved in water or other liquids before use; tablets; soft and hard capsules; syrups; sweets and the like.

Cardiology, Vol. 80 (3–4), 184–95 (M.S. Obsbakken et al.) shows data indicating that pretreatment with cyclocreatine but not creatine provides myocardial protection either during and/or after ischemia. Treatment with cyclocreatine is also stated to function such that mecanical functions are returned after longer episodes of ischemia than treatment with creatine. These are experimental studies in rats.

J. Thorac Cardiovasc. Surg. Vol 87, 1984, 190–200 shows that creatinephosphate has a protecting effect on ischemic cardiac. It is stated in said article at p 197 that phosphocreatine contrary to that previously stated can penetrate the cell membrane, which however is not shown, and also that free creatine does not give a protecting effect.

Thus, it has been known to use phosphocreatine, the creatine analogue cyclocreatine and different creatin precursors in therapeutic situations primarily to protect ischemic tissue.

Phosphocreatine can hardly be used in any therapeutic situations as it cannot pass the intact cell membranes. The positive effects of phosphocreatine on ischemic tissues depend on the fact that the phosphocreatine was taken up by the injured tissue.

Cyclocreatine is a synthetic substance not occuring naturally in the human body. It has been used only in experimental animals. The maximum activity of the creatine quinase action is 350 times lower with phosphorylated cyclocreatine compared to phosphocreatine as substrate. The substance is not used in human subjects and the effect on the central nervous system is unknown.

No studies have been presented showing increased creatine content in human muscle after addit-ion of creatine precursors. The effect of increased precursor content will be dependent on the activities of methylating enzymes in liver and kidneys.

Several publications state that creatine does not bring about any improved medical results. However this depends probably on that the amount as supplied is too low.

Thus, nothing is disclosed or suggested in the above-mentioned prior documents which would lead a man skilled in the art to the findings that the supply of a daily dose of at least 15 g of creatine or 0.2–0.4 g/kg body weight or preferably about 0.3 g/kg body weight administered orally, enterally or parenterally to a mammal having no disorder in the creatine metabolism can be used for preventing the effects of depletion of the muscle phosphoryl creatine store during intensive activity and thereby improve the capacity of the muscles, to prevent muscular fatigue and shorten the recovery phase, or for pre-treatment in connection with heart surgery, to the treatment of anginose patients, respiratory insufficiency, decreased lung function, emphysema, to a patient in need of oxygen treatment, to patients treated with artificial respiration, postoperative and for general malnutrition, for fibromyalgia and to patients with different types of myopathies in order to increase the acutely available energy depots in muscle tissue with limited capacity of glycolytic or mitochondrial energy production. According to Sandstedt et al, Clinical Nutrition, Vol. 10, 1991, pages 97–104, see especially page 101, phosphocreatine levels generally are reduced in muscle tissues after they are subjected to injuries or surgical operations.

Thus, there has been a demand for a safe and simple preparation which without side effects can be given to mammals suffering from the above identified insufficiencies or whose muscular tissue of any reason needs a supply for correct and effective function.

It is known that the creatine phosphagen system plays a central role in energy provision in muscle and other tissue but relatively little is known concerning its uptake and the regulation of the total creatine pool.

There have been a few reports on the effect of creatine supplementation although no direct measurement of the tissue contents of total creatine has been made.

It is also known that depletion of the muscle phosphoryl-creatine store during intensive exercise is commonly associated with the onset of muscle fatigue (Hultman et al; Scand J. Clin. Lab. Invest. 1967, 19, 56–66).

SUMMARY OF THE INVENTION

The object of the present invention is to provide a cheap, simple and safe preparation, without side effects which can be given to mammals having no disorders in their creatine metabolism. Said preparation can be used in connection with the disorders identified above and also to prevent the effects of depletion of the muscle phosphoryl-creatine store during intensive activity and thereby improve the capacity of the muscles and also shorten the recovery phase.

Another object of the present invention is to use creatine for the production of a preparation which supplies such doses to a mammal, that the energy level and work capacity is improved by increasing the muscle performance ability, as well as methods leading to these effects.

These objects are important in conditions where energy rich compounds are limiting, such as post-operative fatigue, respiratory and/or cardiac insufficiency.

The said objects are achieved by the features as defined in the claims.

The said objects are achieved by the features as defined in the claims.

By the enteral or parenteral administration of at least 15 grammes, or 0.2–0.4 g/kg body weight or preferably about 0.3 g/kg body weight, per day of creatine over at least 2 days, without addition of any other active ingredients which might bring about side effects, a maximum creatine level is obtained as well as a surprisingly high plasma concentration.

The administration based on an amount of about 0.3 g of creatine per kg body weight may occur over at least 6 days, however the amounts should be not less than 15 g per day in a 70 kg subject.

By supplementation of 15 to 30 grammes creatine per day over at least 2 days to mammals having no disorders in their creatine metabolism an unexpected increase in the total creatine pool in muscle was obtained without an increase of the plasma creatinine concentration.

The daily supply of creatine is preferably given in several separate doses.

Creatine is preferably supplied in an amount of 15 to 30 grammes, or 0.2–0.4 g/kg body weight or preferably about 0.3 g/kg body weight, per day over 4 to 7 days and may be given in the any form, suitable for enteral or parenteral administration.

For parenteral administration creatine is preferably given in a concentration of 2 to 4 g per 100 ml solution.

Creatine may also be supplied in combination with conventional nutrients such as lipids, carbohydrates, amino acids, electrolytes, trace elements, and vitamins.

PREFERRED EMBODIMENT OF THE INVENTION

If repeated doses of 5 g creatine are supplied every day to a 70 kg subject the blood level can be maintained at 800–1200 μmol per liter blood, i.e. 10–20 times the normal level. Then a rapid uptake of creatine in the muscle tissue takes place over the basal level. The supplying of 20–30 g creatine per day for three to four days gave creatine levels of 120 to 150% of the normal creatine level before the supply, i.e. increases of the concentration of 20 to 50%. These investigations which were carried out with the help of direct measuring of the concentration of creatine in the muscle tissue taken with needle biopsy technique are the only measurements which have been carried out in connection with the supply of creatine to humans. The studies are published in Clinical Science 1992, No. 83, 367–374.

The effect of the increased creatine concentration in muscle has been studied in two series. In a "double blind" study 5 isokinetic maximum exercises were performed before and after a period of one week during which either placebo or creatine was supplied. In the placebo group the power production during the 5 contraction series was unchanged, while significantly higher power was produced in the group which had been supplied with creatine. The creatine and placebo supply respectively was coded, therefore neither the test subjects nor the test supervisor was informed about the nature of the supply until after the study w as completed. The work is published in Clinical Science 1993, No. 84, 556–571.

Additional studies have been made comprising two groups of 1000 meter runners. Also this investigation consisted of a placebo group and a group which was given creatine of the same dosage as above (20–30 g per day for one week). The result was identical, i.e. running times for 4×1000 meters were improved significantly for the group which had been supplied with creatine while it was unchanged for the placebo group. It was established also that in the creatine group the body weight increased by 1.85±0.5 kg while it was unchanged in the placebo group. The body weight increase which was observed also in other groups with the high creatine supply is interpreted as an increased protein synthesis in musculature with high creatine content.

For the tests 5 g creatine H$_2$O (Cr·H$_2$O) was dissolved in 300 ml warm-to-hot water with no detectable formation of creatinine. A dose rate of four times per day was established for 2 subjects and was increased to six times per day in others.

4×5 g for 4½ days (EH and RH$_1$), 7 days (IS and SL) and 10 days (KS).

6×5 g for 7 days (A1, ES and JV, with biopsies on days 3, 5 and 7), and on alternate days for 21 days (HH, HL, JS and OO).

Also included are the results from the control leg of 5 subjects who performed one hour of strenuous exercise per day with collateral leg. Supplementation rates were in this case:

4×5 g for 3½ days (RH$_2$)

6×5 g for 4 days (AT, ML and NC, with biopsies on days 2 and 4) and 7 days (SK).

Subjects have been arranged in order of increasing initial TCr content. Numbers on the graph denote the days of supplementation at the time of biopsy.

■ - female subjects ● - male subjects

Figure 1:
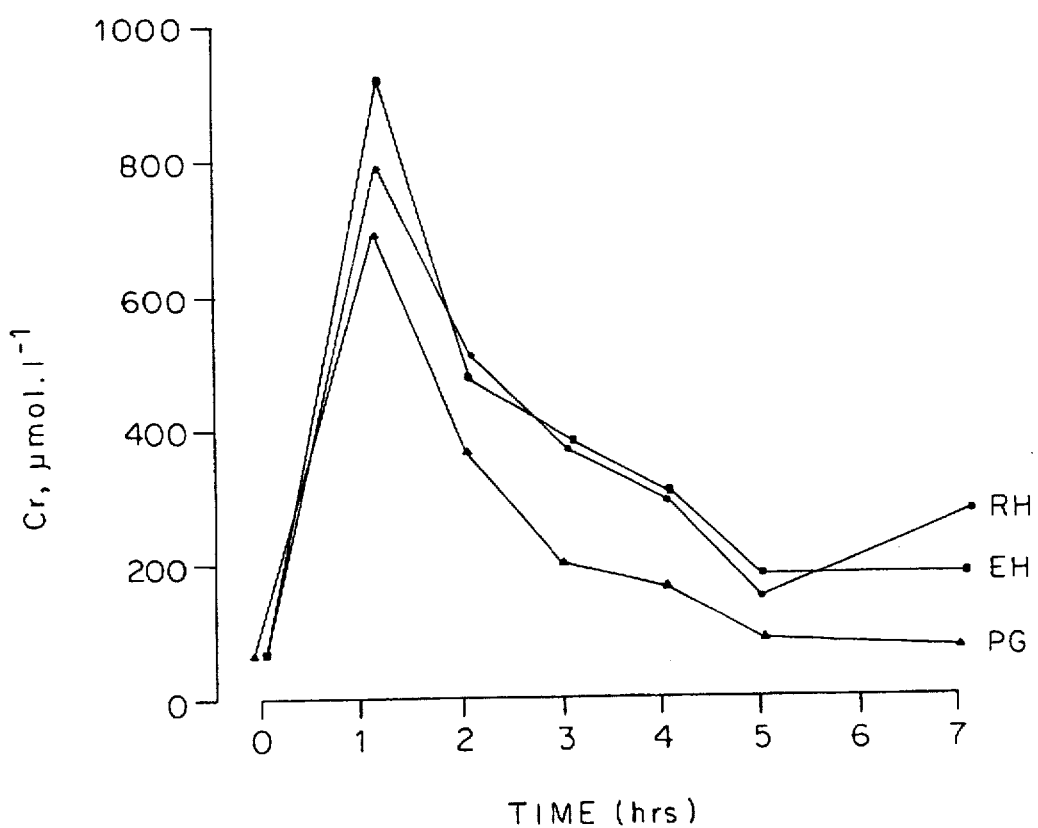
FIG. 1 illustrates a concentration of Cr in the plasma of 3 subjects following a single dose administered at 0 hours of 5 grammes Cr·H$_2$O dissolved in 200 ml warm water. Subjects were aged 28 (PG) to 62 (EH) years and had body weights of 76 kg (RH), 83 kg (PG) and 87 kg (EH).
Figure 2:
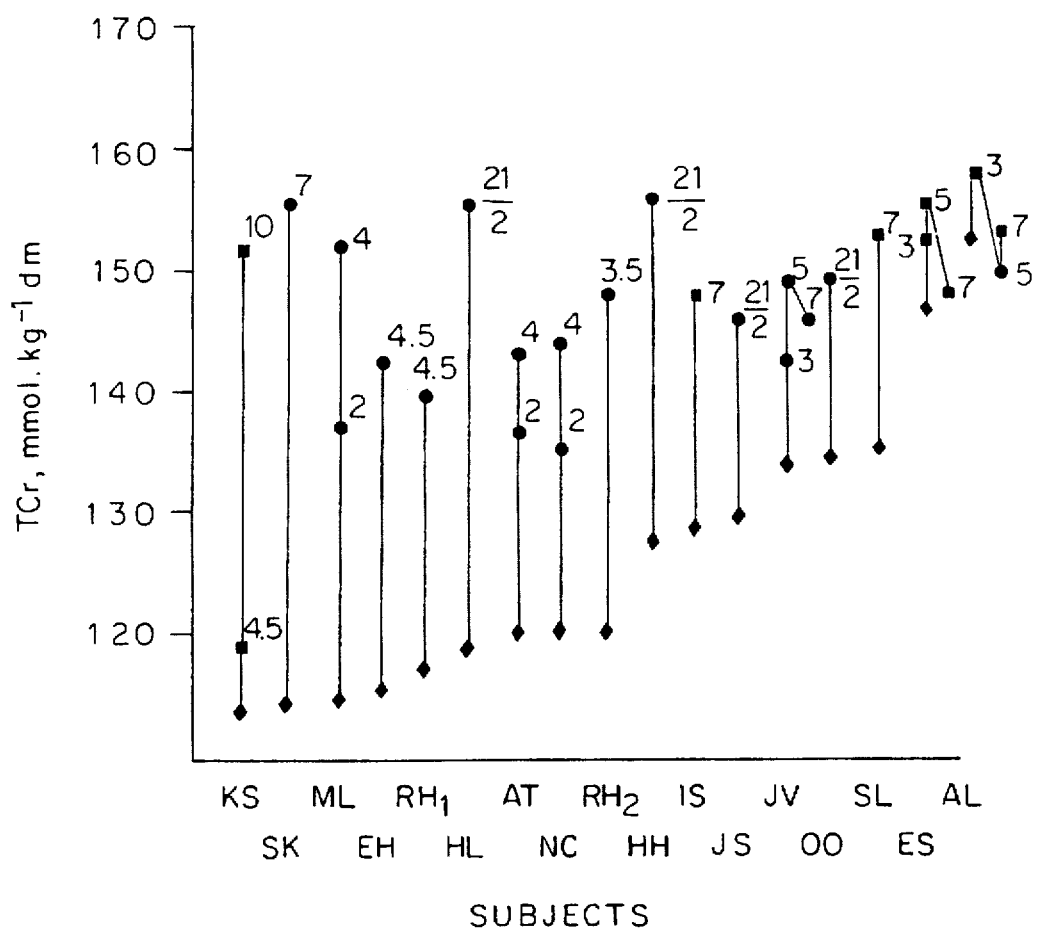
FIG. 2 illustrates the total creatine TCr content of the quadriceps femoris before (♦) and after (■ ,●) supplementation with Cr·H$_2$O.
Figure 3:
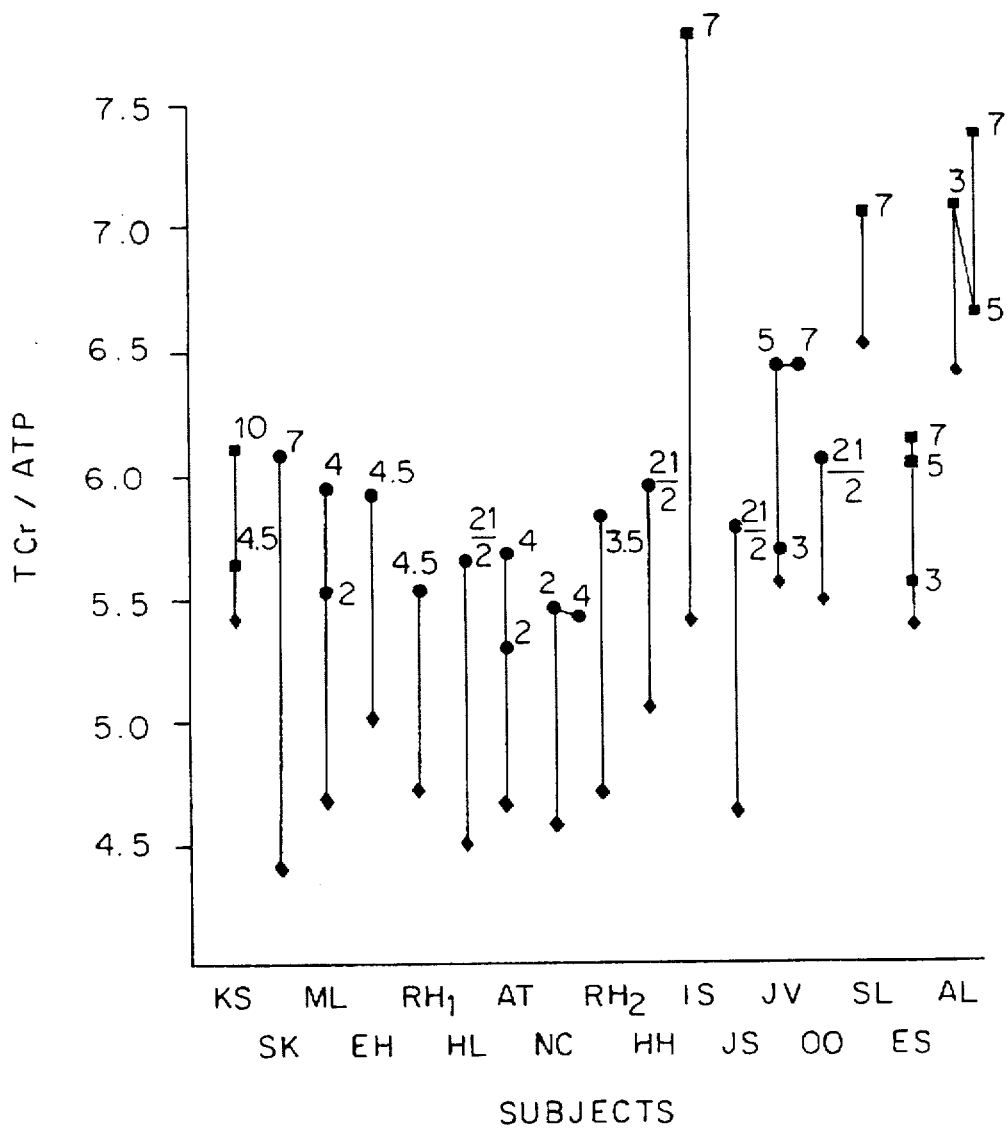

FIG. 3 illustrates the ratio of TCr to ATP contents in biopsy samples of the quadriceps femoris before (♦) and after (■ ,●) supplementation with Cr·H$_2$O. Details of the doses given can be found in the legend to FIG. 2.

■ - female subjects ● - male subjects

Figure 4:
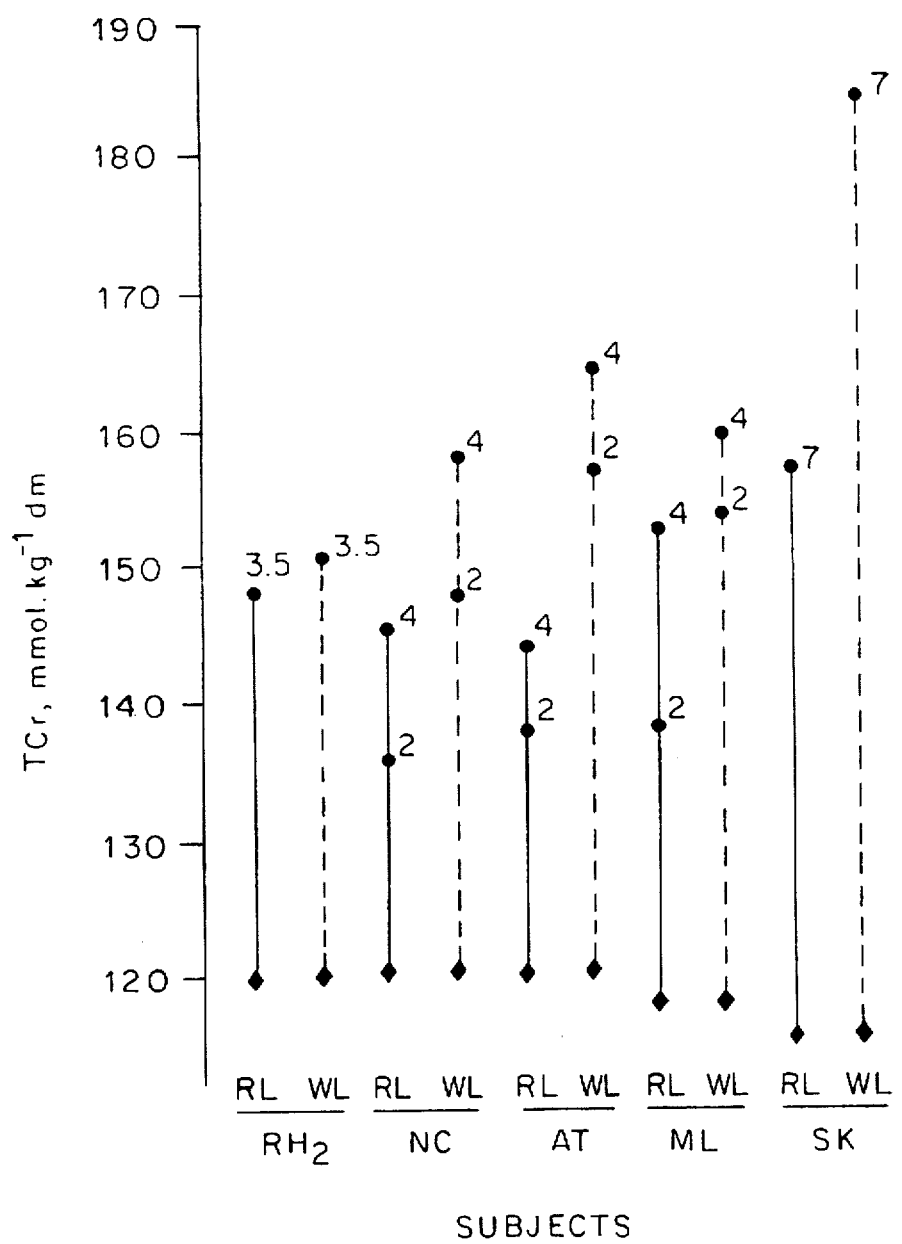

FIG. 4 illustrates the effect of excercise and Cr supplementation upon the TCr content of the quadriceps femoris. During the period of supplementation subjects performed 1 hour of strenuous exercise on a bicycle ergometer using one leg only (Work Leg=WL). During this time the control leg was rested (Rest Leg=RL). For the rest of the time subjects went about their normal daily activities. Dose rates of Cr·H$_2$O used were:

4×5 g for 3½ days (RH$_2$)

6×5 g for 4 days (AT, ML and NC, with biopsies on days 2 and 4) and 7 days (SK).

To minimise the number of biopsies taken, only one was taken prior to supplementation. This was from the rest leg and is assumed to describe also the pre-supplementation TCr-content in the collateral leg. Subjects have been arranged in order of increasing initial TCr-content. All subjects were males. Numbers on the graphs denote the days of supplementation at the time of biopsy. ■ - before and ● - after supplementation.

Figure 5:
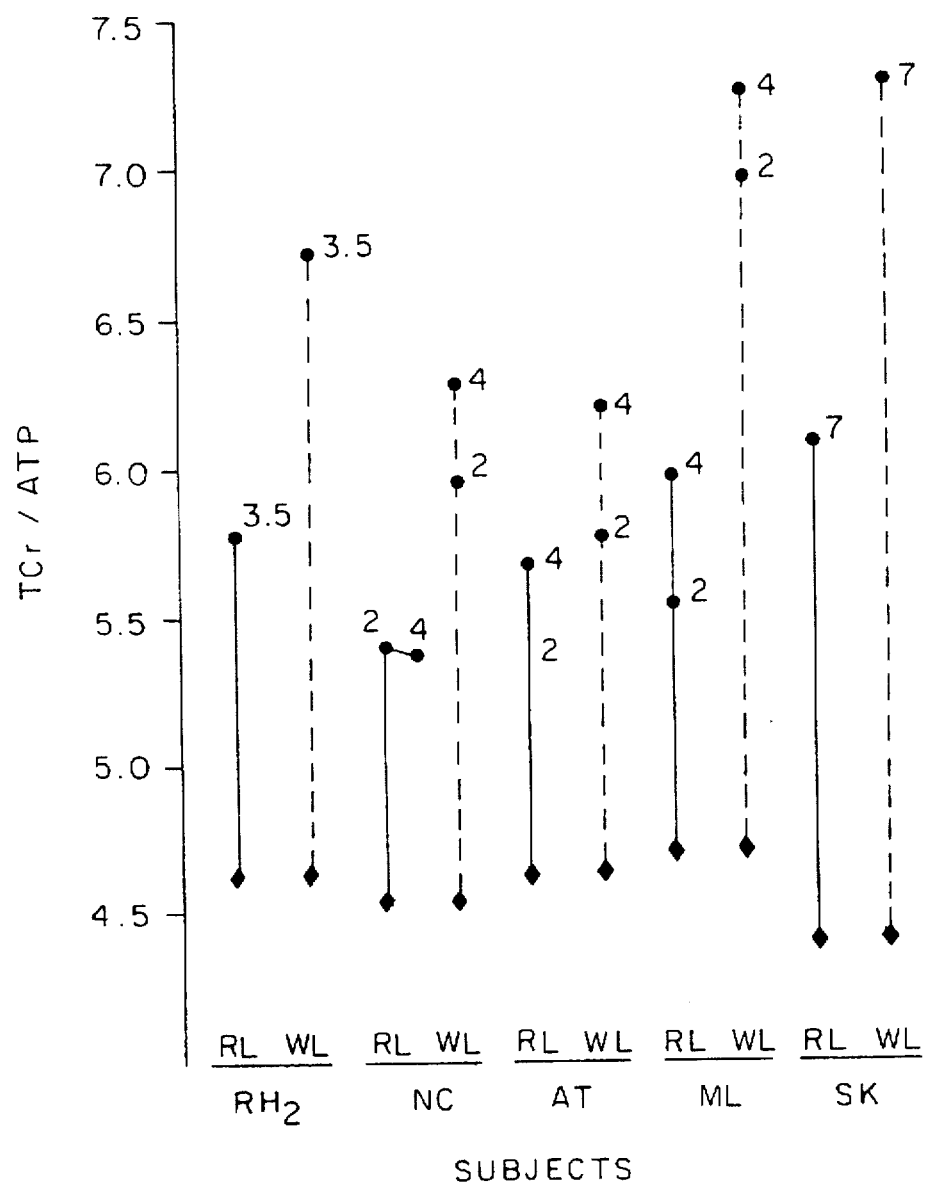

FIG. 5 illustrates the ratio of TCr to ATP contents in biopsy samples of the quadriceps femoris before (♦) and after (●) supplementatio with Cr·H$_2$O in subjects performing an additional 1 hours strenuous exercise per day . RL=rest leg, WL=work leg. Details of the doses given can be found in the legend to FIG. 4.

We claim:

1. A method for increasing the muscle performing capability in mammals having no disorder in creatine metabolism but suffering from or running a risk of depletion of muscle phosphoryl creatine storage comprising administering daily to said mammals, either enterally or parenterally, at least 0.2 g creatine/kg body weight and not less than an amount corresponding to 15 g creatine in a 70 kg mammal.

2. The method according to claim 1 wherein said mammal is administered daily from 15 to 30 grams creatine in a 70 kg. mammal.

3. The method according to claim 1 wherein the mammal is administered daily 0.2–0.4 g creatine/kg body weight.

4. The method according to claim 1 wherein the creatine is administered in combination with conventional nutrients.

5. The method according to claim 4 wherein the conventional nutrients are selected from the group consisting of lipids, carbohydrates, amino acids, electrolytes, trace elements and vitamins.

6. The method according to claim 1 wherein said creatine is administered parenterally in an aqueous solution comprising 2 to 4 grams creatine per 100 ml solution.

7. The method according to claim 6 wherein the aqueous solution further comprises amino acids and glucose.

8. The method according to claim 1 wherein the creatine is administered for at least two days and not more than seven days.

* * * * *